United States Patent [19]

Lattanzi et al.

[11] Patent Number: 4,954,342
[45] Date of Patent: Sep. 4, 1990

[54] PHARMACEUTICAL COMPOSITION FOR INTERARECTAL ADMINISTRATION OF A CALCITONIN AND UNIT DOSAGE FORMS PREPARED THEREFROM

[75] Inventors: Filippo Lattanzi; Riccardo Vanni, both of Siena, Italy

[73] Assignee: Sclavo S.p.A., Siena, Italy

[21] Appl. No.: 249,776

[22] Filed: Sep. 26, 1988

[30] Foreign Application Priority Data

Sep. 25, 1987 [IT] Italy .................. 22031 A/87

[51] Int. Cl.$^5$ .......................... A61K 9/02; A61K 9/48
[52] U.S. Cl. ................................. 424/436; 424/434; 424/451; 424/456
[58] Field of Search ............... 424/436, 111, 456, 451, 424/434

[56] References Cited

U.S. PATENT DOCUMENTS

| | | | |
|---|---|---|---|
| 4,151,276 | 4/1979 | Caulin et al. | 424/111 |
| 4,613,500 | 9/1986 | Suzuki et al. | 514/781 X |
| 4,618,598 | 10/1986 | Conn | 514/6 |
| 4,639,338 | 1/1987 | Stahl et al. | 562/13 |
| 4,711,880 | 12/1987 | Stahl et al. | 514/103 |

FOREIGN PATENT DOCUMENTS 0037943 8/1985 European Pat. Off. .

OTHER PUBLICATIONS

"Enhanced Rectal Absorption of [Asu$^{1,7}$]-eel Calcitonin in Rats Using Polyacrylic Acid Aqueous Gel Base" by Kazuhiro Morimoto et al; Journal of Pharmaceutical Sciences, vol. 73, No. 10, Oct. 1984.
Abstract of Japanese Kokai 118013/81.
Abstract of Japanese Kokai 122309/81.

*Primary Examiner*—Thurman K. Page
*Attorney, Agent, or Firm*—Oblon, Spivak, McClelland, Maier & Neustadt

[57] ABSTRACT

New compositions containing a calcitonin as the active ingredient are described which are suitable for the intrarectal administration as soft gelatin capsules or microenemas, wherein the active principle, optionally admixed with a stabilizer, is dissolved in a liquid vehicle consisting of: (a) at least 70% by weight of a polyethylene or a polypropylene glycol or a mixture of polyethylene or polypropylene glycols with different molecular weights, having the consistency of a homogeneous fluid at room temperature, and (b) less than 15% by weight of a buffer in a pH range of from 4.5 to 6.5, and optionally (c) less than 15% by weight of an alcohol of 2 to 6 carbon atoms containing two or more hydroxy groups.

The new compositions, which do not contain any absorption aid, give calcitonin plasma levels comparable to a conventional intramuscular administration.

28 Claims, No Drawings

PHARMACEUTICAL COMPOSITION FOR INTERARECTAL ADMINISTRATION OF A CALCITONIN AND UNIT DOSAGE FORMS PREPARED THEREFROM

The present invention refers to a new pharmaceutical composition, containing a calcitonin as the active ingredient, suitable for intrarectal administration. A further object of the present invention is a microenema or a soft gelatin capsule prepared therefrom in unit dosage form.

Generally, peptides such as calcitonin, are administered in man by the parenteral route The per-oral administration methods are in fact unfeasible as the proteolytic enzymes which are contained in the gastrointestinal tract, quickly convert these compounds into oligopeptides devoid of pharmacological activity which are eventually metabolized by the liver.

For this reason, calcitonin-containing formulations commercially available are typically for intramuscular or intravenous administration.

Mainly in infants and in the old, which are the subjects more fequently affected by hypercalcemias treatable with calcitonins, and chiefly in the case of long-term treatments, this creates remarkable problems. Therefore, the possibility of administering said active principle intrarectally has been thoroughly investigated in the last few years. Generally, in fact, in the rectal ampulla, drugs do not undergo degradation but are absorbed as such. Furthermore, as most of the absorbed drug enters directly into the general circulation from vena cava, by-passing the liver, it does not undergo the inactivating metabolic action of this organ.

The studies carried out up to now o peptides in general, which have shown that these compounds are not easily absorbed by the rectal walls, and particularly those carried out on calcitonins, that have shown a poor hypercalcemic activity of conventional intrarectal formulations, have led to the conclusions that an absorption aid must be present in intrarectal formulations to provide for satisfactory calcitonin plasma levels.

EP-A-0037943 describes a formulation for the intrarectal administration of peptide hormones (including calcitonins) and polysaccharides, containing an absorption aid selected from ascorbic acid and its salts, a salycilic acid derivative wherein the hydroxy group is esterified, and an acidic amino acid or a derivative thereof.

The examples there reported concerning pharmaceutical compositions containing a calcitonin as the active ingredient, show that :

(a) comparing the claimed intrarectal composition with the intramuscular injection, a dosage unit which is four to five times higher than the i.m. administered one is necessary to get comparable results;

(b) the use of other known absorption aids affords less satisfactory results; and (c) in the absence of absorption aids, an intrarectally administered dose five times higher than a therapeutically effective i.m. dose does not provide for appreciable results.

Other patent applications concerning compositions for the intrarectal administration of a calcitonin are for instance Japanese patent application publications nos. 118013/81 and 122309/81 (Derwent cards Farmdoc 81-80457D and 81-82491D), and Dutch patent application 299/86, which claim the use of particular absorption aids for intrarectal compositions.

Furthermore, the Journal of Pharmaceutical Sciences, 73(10), (1984), pages 1366–8, describes a composition containing a calcitonin in a polyacrylic acid gel base. The experimental data there reported, which show that such a composition significantly improves the absorption of the peptide through the rectal walls, also show that a dose which is about 35 times the i.m. dose is necessary to provide for equivalent effects. In the same literature reference, the poor results obtained with a formulation containing a calcitonin disperded in polyethylene glycol 1000 are reported It has now surprisingly been found and it does represent a first object of the present invention, that it is possible to prepare a composition, containing a calcitonin as the active ingredient, suitable for the preparation of dosage unit forms for intrarectal administration which allow the almost complete absorption of the active ingredient, without using any absorption aid.

More particularly, the composition of the present invention consists of a solution of the active principle, optionally admixed with a suitable stabilizer, in a vehicle, liquid at room temperature, consisting of :

(a) at least 70 % by weight of a polyethylene or polypropylene glycol or a mixture of polyethylene or polypropylene glycols with different molecular weights, having the consistency of a homogeneous fluid at room temperature, and (b) less than 15 % by weight of a physiologically acceptable aqueous buffer in a pH range of from 4.5 to 6.5, and, optionally, (c) less than 15 % by weight of an alcohol of from 2 to 6 carbon atoms containing two or more hydroxy groups.

(The above percentages by weight are based on the weight of the final composition.)

The composition of the present invention is used in the preparation of microenemas and soft gelatin capsules, employed as unit dosage forms.

Said unit dosage forms, prepared from the above composition and generally containing from 50 to 500 IU of a calcitonin as the active ingredient, represent a further object of the present invention.

As for the active principle which can suitably be employed in the formulation of the present invention, this can be any of the known natural and synthetic calcitonins, such as for instance salmon calcitonin (SCT), eel calcitonin (ECT), porcine calcitonin, or the synthetic analogs thereof, such as [Asu$^{1-7}$[ECT (carbocalcitonin), etc..

The amount of active principle in the composition will obviously depend on the desired amount of calcitonin per unit dosage form and on the total volume of the unit dosage form.

Typically, however, compositions containing from 20 to 800 IU of active principle per ml of vehicle, can suitably be used.

In some cases, particularly when eel calcitonin is employed as the active principle, it may be advisable or necessary to use a stabilizer. A particularly preferred stabilizer, as described in EP-A-249,811, is human albumin, which proved to be quite effective both to increase the intrinsic stability of calcitonin and to control its adsorption on the walls of the glass or plastic containers used in the formulation process. If used, said stabilizer will be contained in the composition in an amount comprised between 0.01 and 1.2 mg, and preferably, between 0.05 and 1.0 mg, per calcitonin IU.

The polyethylene or polypropylene glycol or the mixture of polyethylene or polypropylene glycols with different molecular weights which can be used as the vehicle base in the composition of the present invention, must be a homogeneous fluid at room temperature.

It will therefore consist of one or more polyethylene or polypropylene glycols with a low molecular weight, generally comprised between 200 and 600, and preferably comprised between 200 and 400, optionally containing minor amounts of polyethylene or polypropylene glycols with higher molecular weight in suitable proportions to provide for a vehicle fluid and homogeneous at room temperature.

According to a preferred embodiment of the present invention, said polyalkylene glycol or polyalkylene glycol mixture will be present in an amount, by weight, higher than 75 %, and, according to a most preferred embodiment, higher than 80 %.

Furthermore, depending on the particularly desired dosage unit form, either a microenema or a soft gelatin capsule, also the type of polyalkylene glycol which can be used will vary. In particular, when the composition of the present invention has to be employed for the preparation of a soft gelatin capsule, polypropylene glycol will not be used as it is known that this compound is capable of attacking the capsule gelatin shell. In such a case a polyethylene glycol or a mixture of polyethylene glycols has to be employed. Suitable alcohols, optionally present, as single compounds or mixtures thereof, in a percentage, by weight, lower than 15 %, and, according to a preferred embodiment, lower than 10 %, are propylene glycol, ethylene glycol, sorbitol, and, preferably, glycerin. Said alcohols are normally present when the composition has to be used for the preparation of soft gelatin capsules, while it can be avoided in the preparation of microenemas.

Physiologically acceptable aqueous buffers, in a pH range of from 4.5 to 6.5, which can suitably be employed in the composition of the present invention are phosphate buffers, citrate buffers, etc..

Considering also the desired hypercalcemic activity, preferred buffers are however based on mono- or dibasic sodium or potassium phosphates, optionally mixed with citric acid.

Said buffer will be present in a percentage, by weight, lower than 15 % and, preferably, comprised between 3 and 12 %.

The composition of the present invention is suitably employed for the preparation of microenemas or soft gelatin capsules, typically containing a volume comprised between 0.6 and 2.5 ml, in the case of a capsule, and between 2.5 and 10 ml, in the case of a microenema, according to conventional techniques well known to the art skilled technician or according to methods described in the open and patent literature. As an example, as for the capsules, the gelatin shell may suitably be prepared according to the teachings of EP-A-120248 and EP-A-121321.

The following examples are aimed at further illustrating the preparation of some representative compositions and unit dosage forms of the present invention and the results which have been obtained by the intrarectal administration thereof.

Example 1

Rectal soft gelatin capsules manufactured by Scherer, are filled with the following composition (the amounts listed hereinbelow refer to the preparation of a single capsule):

| ECT | 100 IU |
|---|---|
| glycerin | 50 mg |
| polyethylene glycol 400 | 400 mg |
| phosphate buffer pH 6 | 50 mg |

Said capsules are administered to a group of five healthy volunteers and 30, 60, and 120 minutes later, RIA dosing of plasma ECT is carried out.

To a different group of five healthy volunteers, used as control, an equal dosage (100 IU) of eel calcitonin is administered i.m.. Also in this case, 30, 60, and 120 minutes later, RIA dosing of plasma calcitonin is carried out and the results, as the average of each group, are reported in following Table I

TABLE I

| Administration route | Plasma ECT (pg/ml) | | |
|---|---|---|---|
| | 30' | 60' | 120' |
| rectal | 275 | 250 | 200 |
| intramuscular | 75 | 150 | 100 |

Example 2

Soft gelatin capsules manufactured by Scherer are filled with the following composition (the amounts listed hereinbelow refer to the preparation of a single capsule):

| ECT | 100 IU |
|---|---|
| glycerin | 50 mg |
| polyethylene glycol 200 | 440 mg |
| phosphate buffer pH 6 | 50 mg |
| human albumin | 5 mg |

Said capsules are administered to a group of four healthy volunteers and 15, 30, 60, 120, and 180 minutes later, RIA dosing of plasma ECT is carried out.

To a different group of four healthy volunteers, employed as control, an equal dose (100 IU) of ECT is administered i.m.. Also in this case, RIA dosing of plasma ECT is carried out and the results as the average of each group are reported in following Table II

TABLE II

| Administration route | Plasma ECT (pg/ml) | | | | |
|---|---|---|---|---|---|
| | 15' | 30' | 60' | 120' | 180' |
| rectal | 547 | 607 | 454 | 290 | 250 |
| intramuscular | 594 | 728 | 433 | 387 | 240 |

Example 3

Soft gelatin capsules manufactured by Scherer are filled with the same composition as in the foregoing example but containing 50 IU instead of 100 IU of eel calcitonin per unit.

The capsules are administered to a group of five healthy volunteers and 15, 30, 60, 120, and 180 minutes later, plasma calcium levels are measured. The same dose of eel calcitonin is administered i.m. to another group of five healthy volunteers and also in this case plasma calcium levels are measured at the same times. The results are reported in following Table III :

TABLE III

| Administration route | Plasma calcium levels (mg/ml) | | | | | |
|---|---|---|---|---|---|---|
| | 0' | 15' | 30' | 60' | 120' | 180' |
| rectal | 9.02 | 8.94 | 8.66 | 8.68 | 8.68 | 8.74 |
| intramusc. | 8.98 | 8.78 | 8.64 | 8.34 | 8.52 | 8.78 |

Examples 4-10

The following examples describe some compositions containing a calcitonin as the active ingredient, which can be employed for intrarectal administration as soft gelatin capsules. The amounts indicated refer to a composition suitable for the preparation of 1000 capsules

| (4) | ECT | 100,000 IU |
|---|---|---|
| | glycerin | 40 g |
| | polyethylene glycol 200 | 450 g |
| | phosphate-citrate buffer pH 4.6 | 60 g |
| | human albumin | 10 g |
| (5) | ECT | 150,000 IU |
| | glycerin | 40 g |
| | polyethylene glycol 200 | 450 g |
| | polyethylene glycol 400 | 250 g |
| | polyethylene glycol 4000 | 50 g |
| | phosphate-citrate buffer pH 4.6 | 60 g |
| | human albumin | 15 g |
| (6) | ECT | 200,000 IU |
| | glycerin | 80 g |
| | polyethylene glycol 200 | 850 g |
| | polyethylene glycol 4000 | 80 g |
| | phosphate-citrate buffer pH 4.6 | 100 g |
| | human albumin | 20 g |
| (7) | SCT | 100,000 IU |
| | glycerin | 40 g |
| | polyethylene glycol 200 | 450 g |
| | phosphate buffer pH 6.0 | 60 g |
| (8) | SCT | 150,000 IU |
| | glycerin | 40 g |
| | polyethylene glycol 200 | 500 g |
| | polyethylene glycol 400 | 250 g |
| | polyethylene glycol 4000 | 50 g |
| | phosphate-citrate buffer pH 4.6 | 60 g |
| | human albumin | 10 g |
| (9) | ECT | 100,000 IU |
| | glycerin | 50 g |
| | sorbitol | 10 g |
| | polyethylene glycol 200 | 900 g |
| | polyethylene glycol 4000 | 80 g |
| | phosphate-citrate buffer pH 4.6 | 90 g |
| | human albumin | 10 g |
| (10) | [Asu$^{1-7}$]ECT | 150,000 IU |
| | glycerin | 60 g |
| | polyethylene glycol 200 | 650 g |
| | polyethylene glycol 400 | 250 g |
| | polyethylene glycol 4000 | 50 g |
| | phosphate-citrate buffer pH 4.6 | 100 g |
| | human albumin | 15 g |

Examples 11-14

The following examples refer to compositions containing a calcitonin as the active ingredient, which can be administered intrarectally as microenemas. The indicated amounts refer to a composition suitable for the preparation of 1000 microenemas.

| (11) | ECT | 150,000 IU |
|---|---|---|
| | glycerin | 100 g |
| | sorbitol | 300 g |
| | polyethylene glycol 200 | 5000 g |
| | phosphate buffer pH 6.0 | 500 g |
| | human albumin | 20 g |
| (12) | ECT | 200,000 IU |
| | glycerin | 50 g |
| | sorbitol | 250 g |
| | polyethylene glycol 200 | 2000 g |
| | polyethylene glycol 400 | 2000 g |
| | polyethylene glycol 4000 | 200 g |
| | phosphate-citrate buffer pH 4.6 | 300 g |
| | human albumin | 20 g |
| (13) | SCT | 100,000 IU |
| | sorbitol | 350 g |
| | polyethylene glycol 200 | 5000 g |
| | phosphate buffer pH 6 | 500 g |
| (14) | [Asu$^{1-7}$]ECT | 150,000 IU |
| | glycerin | 40 g |
| | sorbitol | 300 g |
| | polyethylene glycol 200 | 2500 g |
| | polyethylene glycol 400 | 2000 g |
| | polyethylene glycol 4000 | 250 g |
| | phosphate-citrate buffer pH 4.6 | 400 g |
| | human albumin | 15 g |

What is claimed as new and desired to be secured by letters patent of the U.S. is:

1. A pharmaceutical composition containing a calcitonin as the active ingredient and suitable for the preparation of capsules for intrarectal administration or microenemas, said composition comprising a calcitonin dissolved in a liquid vehicle comprising:
   (a) at least 70% by weight of a polyethylene or polypropylene glycol or a mixture of polyethylene or polypropylene glycols of different molecular weights, having the consistency of a homogeneous fluid at room temperature, and
   (b) less than 15% by weight of a physiologically acceptable aqueous buffer having a pH range of from 4.5 to 6.5.

2. The composition of claim 1, wherein said composition comprises a stabilizer and said vehicle comprises:
   (c) less than 15% by weight of an alcohol of from 2 to 6 carbon atoms containing two or more hydroxy groups.

3. The composition of claim 1, wherein the polyethylene or polypropylene glycol or the mixture of polyethylene or polypropylene glycols is present in an amount, by weight, higher than 75%.

4. The composition of claim 1, wherein the polyethylene or polypropylene glycol or the mixture of polyethylene or polypropylene glycols is present in an amount, by weight, higher than 80%.

5. The composition of claim 1, wherein the aqueous buffer is present in an amount, by weight, of between 3% and 12%.

6. The composition of claim 2, wherein the alcohol present in the liquid vehicle is selected from the group consisting of propylene glycol, ethylene glycol, sorbitol, glycerin, and mixtures thereof.

7. The composition of claim 2, wherein the alcohol present in the liquid vehicle is present in an amount lower than 10% by weight.

8. The composition of claim 2, wherein the stabilizer is human albumin.

9. The composition of claim 8, wherein the albumin is present in an amount comprised between 0.01 and 1.2 mg per calcitonin IU.

10. The composition of claim 1, wherein the aqueous buffer is phosphate-citrate buffer having a pH of 4.6.

11. The composition of claim 1, wherein the calcitonin is eel calcitonin.

12. The composition of claim 1, containing from 20 to 800 IU of calcitonin per ml of vehicle.

13. A unit dosage form suitable for intrarectal administration as a microenema or a soft gelatin capsule, prepared from a composition comprising a calcitonin dissolved in a liquid vehicle comprising:
   (a) at least 70% by weight of a polyethylene or polypropylene glycol or a mixture of polyethylene or polypropylene glycols of different molecular weights, having the consistency of a homogeneous fluid at room temperature, and
   (b) less than 15% by weight of a physiologically acceptable aqueous buffer in a pH range of from 4.5 to 6.5.

14. The unit dosage form of claim 13, wherein said composition comprises a stabilizer and said vehicle comprises:
   (c) less than 15% by weight of an alcohol of from 2 to 6 carbon atoms containing two or more hydroxy groups.

15. The unit dosage form of claim 13, wherein the polyethylene or polypropylene glycol or the mixture of polyethylene or polypropylene glycols is present in an amount, by weight, higher than 75%.

16. The unit dosage form of claim 14, wherein the polyethylene or polypropylene glycol or the mixture of polyethylene or polypropylene glycols is present in an amount, by weight, higher than 80%.

17. The unit dosage form of claim 13, wherein the aqueous buffer is present in an amount, by weight, of between 3% and 12%.

18. The unit dosage form of claim 14, wherein the alcohol present in the liquid vehicle is selected from the group consisting of propylene glycol, ethylene glycol, sorbitol, glycerin, and mixtures thereof.

19. The unit dosage form of claim 14, wherein the alcohol present in the liquid vehicle is present in an amount lower than 10% by weight.

20. The unit dosage form of claim 14, wherein the stabilizer is human albumin.

21. The unit dosage form of claim 20, wherein the albumin is present in an amount of between 0.01 and 1.2 mg per calcitonin IU.

22. The unit dosage form of claim 14, wherein the aqueous buffer is phosphate-citrate buffer having a pH of 4.6.

23. The unit dosage form of claim 14, wherein the calcitonin is eel calcitonin.

24. The unit dosage form of claim 14, characterized in that it contains from 20 to 800 IU of calcitonin per ml of vehicle.

25. The unit dosage form of claim 14, containing from 50 to 500 IU of a calcitonin.

26. A soft gelatin capsule for the intrarectal administration of a calcitonin, comprising:
   (a) from 50 to 500 IU of a calcitonin.
   (b) a polyethylene glycol or a mixture of polyethylene glycols of different molecular weights, having the consistency of a homogeneous fluid at room temperature, in an amount, by weight, higher than 75% based on the overall weight of the capsule fill; and
   (c) a physiologically acceptable buffer having a pH range of from 4.5 to 6.5, in an amount, by weight, comprised between 3% and 12% based on the overall weight of the capsule fill.

27. The soft gelatin capsule of claim 26, comprising said calcitonin admixed with from 0.01 to 1.2 mg of human albumin per calcitonin IU, and
   (d) an alcohol of from 2 to 6 carbon atoms, containing two or more hydroxy groups, in an amount, by weight, lower than 10% based on the overall weight of the capsule fill.

28. the capsule of claim 26, wherein the alcohol (d) is glycerin.

* * * * *